United States Patent [19]

Moreno et al.

[11] Patent Number: 5,489,267
[45] Date of Patent: *Feb. 6, 1996

[54] DOUBLE CHAMBER DISPOSABLE SYRINGE

[76] Inventors: Saul Moreno; Jaime L. Szapiro; Leonardo Szames, all of Tabare 1641, Buenos Aires, Argentina

[*] Notice: The term of this patent shall not extend beyond the expiration date of Pat. No. 5,395,325.

[21] Appl. No.: 275,231

[22] Filed: Jul. 14, 1994

Related U.S. Application Data

[63] Continuation-in-part of Ser. No. 176,470, Jan. 3, 1994, Pat. No. 5,395,325.

[51] Int. Cl.$^6$ .................................................. A61M 5/00
[52] U.S. Cl. .................................................. 604/89; 604/191
[58] Field of Search .................................. 604/89, 88, 87, 604/86, 110, 187, 191, 198, 218, 231, 232

[56] References Cited

U.S. PATENT DOCUMENTS

| | | | |
|---|---|---|---|
| 4,702,737 | 10/1987 | Pizzino | 604/191 |
| 4,886,495 | 12/1989 | Reynolds | 604/88 |
| 4,941,876 | 7/1990 | Meyer et al. | 604/89 |
| 4,969,877 | 11/1990 | Kornberg | 604/198 X |
| 5,015,229 | 5/1991 | Meyer et al. | 604/191 X |
| 5,395,325 | 3/1995 | Moreno et al. | 604/89 |

*Primary Examiner*—John D. Yasko
*Attorney, Agent, or Firm*—Bachman & LaPointe

[57] ABSTRACT

A double chamber disposable syringe includes a main hollow body having an inner diameter and engaged with an injection needle. A second hollow body is included having an outer diameter smaller than the inner diameter of the main body and having an open lower end and an upper end. The upper end defines a plugging end. A plunger projects through the open lower end of the second hollow body. The second hollow body is positioned between the main body and the plunger. A plug is engaged with the inner diameter of the main body and located adjacent the plugging end. The plug and the plugging end have conduits in substantial alignment wherein the conduit of the plug leads into the main body and the conduit of the plugging end leads into the second body. A cylindrical needle cover extends from the main body and is slidably engaged therewith for enclosing the needle. A sheet means utilized for separating the conduits of the plug and plugging end is positioned between the conduits of the plug and plugging end. The sheet is penetrable via the pressure created by the plunger in the second body.

9 Claims, 2 Drawing Sheets

DOUBLE CHAMBER DISPOSABLE SYRINGE

CROSS REFERENCES TO RELATED APPLICATIONS

This application is a continuation-in-part of the Application having Ser. No. 176,470, filed Jan. 3, 1994 now U.S. Pat. No. 5,395,325.

FIELD OF THE INVENTION

The instant invention relates to a double chamber disposable syringe, and more particularly, to a syringe for the simultaneous mixture and administration of a drug, having means for mixing the contents of the chambers without contaminating the mixture via foreign particles.

BACKGROUND OF THE INVENTION

Double chamber syringes typically include a first chamber having a powdered drug therein and a second chamber having a diluting substance. Before using the syringe, the powdered drug and the diluting substance must be mixed. The first and second chambers respectively containing the powdered drug and diluting substance are usually separated by a septum or the like which is adapted to be breached by a needle or the like located in the internal mechanism of the syringe. Therefore, prior to injection, the chambers are moved relative to each other and an internally located pin is forced into the septum causing the same to be breached. As a result, the diluting substance of the first chamber is caused to mix with the powdered drug. Thereafter, the syringe is used to inject the mixture into the patient.

Because the septums or the like are breached with a sharply pointed instrument, small parts of the septum, usually formed from rubber, are caused to leach into the mixture. Consequently, the mixture having the rubber contaminant is injected into a patient and tests have shown that such contaminants can be physically harmful to humans. A plurality of differently designed syringes are available which use a sharp instrument for breaching a septum for the mixture of substances to be injected into a patient. None of these devices consider the possibility of or take measures to forestall contamination via particles broken from septums.

U.S. Pat. No. 4,886,495 to Reynolds discloses a pre-filled syringe for use with one or two component medicaments which uses a vial containing a medicament, or at least one component of a medicament, wherein the vial has an open bottom which engages a piston. The piston is coupled with a plunger and an adapter cap having an internal needle. An external connection for a needle is placed over a cap on the vial, causing the assembly to be converted into a pre-filled syringe. The piston has an axial passage closed by a resealable septum. A separate diluent stored in a flexible capsule may be introduced into the vial through the piston by a double ended needle mounted on a further cap attached to the capsule. The further cap is coupled within the tubular interior of the plunger so that the double ended needle penetrates the septum in the piston. The capsule is pushed forward onto the double ended needle when its contents are to be expelled into the vial. The capsule and its cap are then removed and discarded. Because a sharp pointed needle is used for breaching the septum, as discussed above, contaminants comprised of particles of the septum are prone to enter the medicament, possibly resulting in harm to the medicament user.

U.S. Pat. No. 4,702,737 discloses a dual dose syringe. The syringe includes a barrel comprising a plurality of telescoping sections of progressively decreasing diameter. A puncturable fluid tight membrane extends across the forward end of each barrel section, with exception to the first, and divides the interior of the barrel into a plurality of separate fluid receiving chambers. Each of the chambers may contain a different fluid medication. A plunger is slidably mounted in the last barrel section and extends exteriorly therefrom. At the forward end of the syringe is a hollow needle, which extends through a needle receiving tubular conduit at the forward end of the first barrel section so that the needle is disposed partly inside and partly outside the barrel. Both ends of the needle are sharply pointed. The inner end of the needle is adapted to puncture the membrane so that as each chamber in the barrel is emptied, the next chamber is placed in communication with the needle. As indicated above, such puncturing of the membrane can cause particles of the membrane to leach into the mixture to be injected. Accordingly, the mixture with the contaminants are injected into the medication receiver, possibly having ill effects.

There exist a need, therefore, for a syringe having a septum or the like for separating different components of a medication which is breachable via the internal mechanism of the syringe yet does not risk contamination of the medication in the syringe with small particles of the septum.

SUMMARY OF THE INVENTION

The object of this invention is to provide a double chamber syringe having means for mixing substances in the chambers without contaminating the resulting mixture.

Another object of this invention is to provide a double chamber syringe wherein the chambers are separated by a pressure breachable sheet.

Yet another object of this invention is to provide a double chamber syringe having a pressure breachable sheet extending between the chambers, wherein the syringe includes an internal design for directing a fluid under high pressure at the sheet for breaching the same.

The foregoing objects are attained by the double chamber disposable syringe of the present invention which includes a main hollow body having an inner diameter and engaged with an injection needle. A second hollow body is included having an outer diameter smaller than the inner diameter of the main body and having an open lower end and an upper end. The upper end defines a plugging means. The second hollow body is adapted to be moved relative the main body. A plunger means projects through the open lower end of the second hollow body. The second hollow body is positioned between the main body and the plunger means. A plug is engaged with the inner diameter of the main body and located adjacent the plugging means. The plug and the plugging means have conduits in substantial alignment wherein the conduit of the plug leads into the main body and the conduit of the plugging means leads into the second body. A sheet means is utilized for separating the conduits of the plug and plugging means and is positioned therebetween. The sheet means is penetrable via the pressure created by the plunger means in the second body. The syringe may also include an additional sheet means positioned between the main hollow body and the needle.

The details of the present invention are set out in the following description and drawings wherein like reference characters depict like elements.

DETAILED DESCRIPTION OF THE PREFERRED EMBODIMENT

Figure 1:
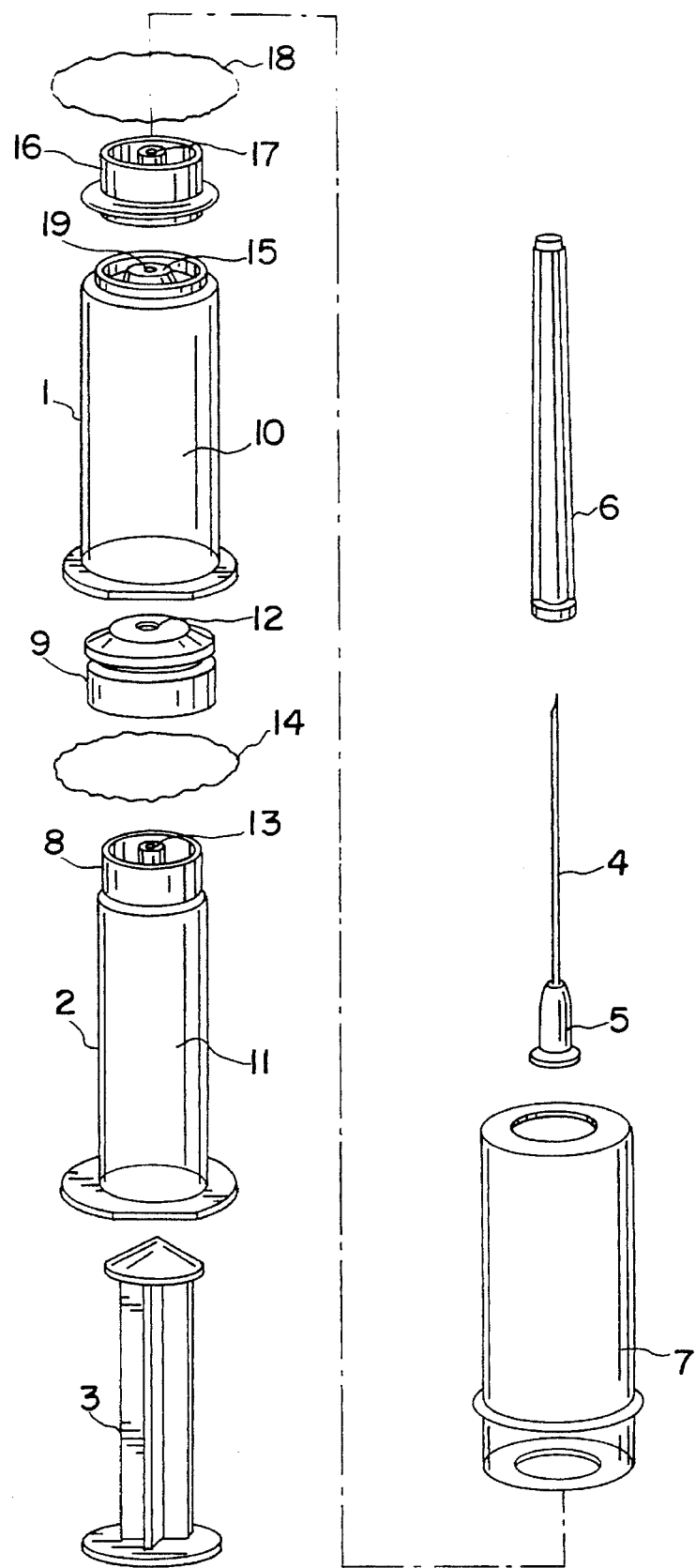
FIG. 1 is a schematic and exploded perspective view of a syringe in accordance with the principles of the present invention.

Referring now to the drawings in detail, there is shown in FIG. 1 the syringe of the present invention which is generally comprised of a main hollow body 1, a second slidable hollow body 2, a thrust plunger 3, an injection needle 4, having a plugging cone 5 and sheath 6, and a needle cover skirt 7 slidable relative to the hollow chamber body 1.

Figure 2:
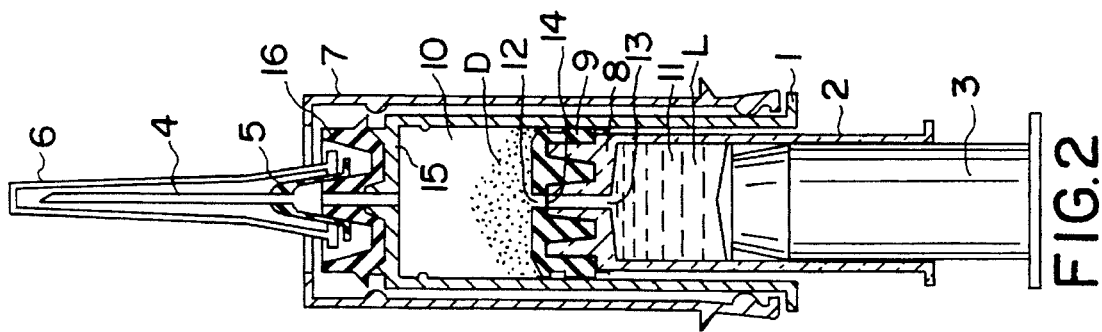
FIG. 2 is a schematic longitudinal section of the syringe of FIG. 1, showing the arrangement of the elements forming the syringe, before use.

The two chambers 10 and 11 are preferably pre-filled with a powdered drug and a diluent, respectively. As shown in FIG. 2, the syringe of the present invention may be marketed with the medicine already contained therein, e.g., a powdered drug D inside chamber 10 and a diluent liquid L inside chamber 11. The syringe, however, may also be used with different substances as required.

Referring to FIG. 1, in order for the assembly to operate properly, the upper base of the secondary hollow body 2 has a coupling head 8 wherein elastomeric plug 9 is press-fitted. Plug 9 also fits tightly but slidingly in the cylindrical wall of the main body 1. Plug 9 serves as supporting means for the secondary body 2, relative main body 1, and plunger 3 and also as a divider between both chambers 10 and 11.

Plug 9, as well as the coupling head 8, have corresponding and aligned coaxial conduits 12 and 13 for establishing fluid communication between chambers 10 and 11. The conduits are separated by a sheet 14, which segregate products D and L into their corresponding chambers, as shown in FIG. 2, prior to being mixed for injection.

Similar to secondary body 2, main body 1 includes a coupling head 15 having a conduit 19 and positioned between the plugging cone 5 of needle 4 and main body 1, as shown in FIG. 1. Coupling head 15 is attached to a second elastomeric plug 16 having a coaxial conduit 17 corresponding to and in alignment with a conduit in coupling head 15. Elastomeric plug 16 is connected with plugging cone 5. A second sheet 18 is positioned between second elastomeric plug 16 and coupling head 15. As with sheet 14, second sheet 18 is breachable via pressure created in the syringe, but in this case, by second body 2 moving through main body 1. Accordingly, the sheets 14 and 18 are formed from a material which will breach under the pressure created by movement through chambers 11 and 10, respectively, of pressurized fluid L, as shown in FIG. 2, from the large cavity of chamber 11 into the small cavity of conduit 13 and from the large cavity of chamber 10 into the small cavity of conduit 19, respectively. A rubber material of proper thickness for breaking in accordance with the amount pressure build up attained, may be used for forming sheets 14 and 18.

For breaching both sheets 14 and 18, the pressure created by the plunger is enhanced by the internal design of the syringe. Fluid L (see FIG. 2) is forced via plunger 3 through chamber 11 into conduit 13 of coupling head 8, wherein chamber 11 has a substantially larger diameter than conduit 13. As a result of this diameter differential, fluid L (see FIG. 2) is caused to gain force and velocity as it is forced through conduit 13. This increased force and velocity creates a pressure against sheet 14 sufficient to breach sheet 14. Chamber 10 and coupling head 15 having conduit 19 are similarly designed for achieving the same results with relation to sheet 18 except that the pressure is created by the movement of the secondary hollow body 2 and plug 9 through main hollow body 1.

Figure 3:
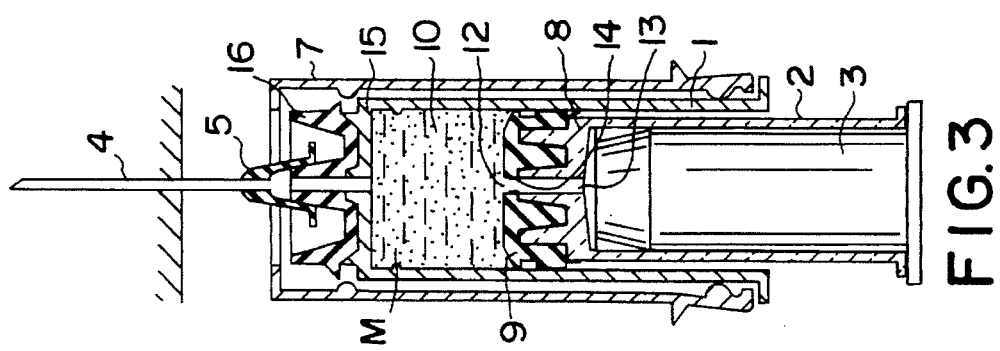
FIG. 3 is a sectional view similar to that of FIG. 2 showing the arrangement of the elements forming the syringe once a mixture is produced, and the breaching of a sheet separating the chambers.

Referring to FIGS. 2–5, in operation, and before injecting the drug, plunger 3 is displaced, compressing liquid L until separating sheet 14 collapses, under pressure created by plunger 3 moving diluent L through conduit 13 and at the area between the two coaxial conduits 12 and 13. Plunger 3 should be displaced until head 15 abuts the upper base of secondary body 2 so that leak or feedback of the mixture M now contained in the chamber 10 is prevented, as shown in FIG. 3.

Once the mixture is in chamber 10, the user stirs the syringe until the drug D is wholly diluted. By compressing the plunger further, and accordingly, second hollow body 2, a second pressure is developed in the main body and conduit 19 for collapsing the second separating sheet 18 positioned between plug 16 and head 15. The user may then conventionally inject the medicine, i.e., displace plunger 3 and second hollow body 2 relative to main body 1. The elastomeric plug 9 acts as a pushing head, as shown in FIG. 3.

Figure 5:
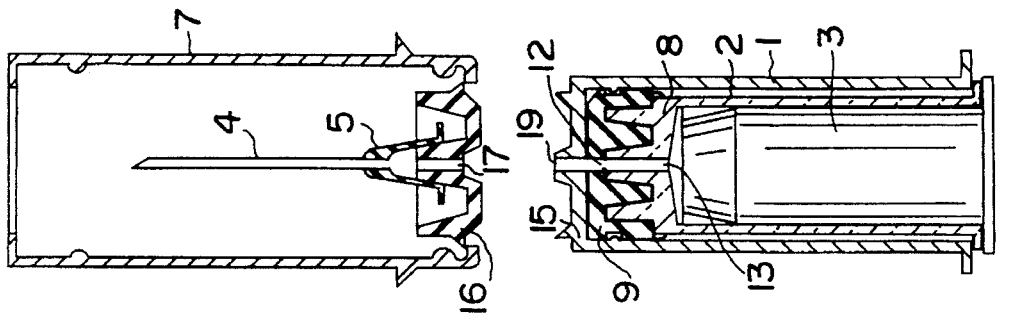
FIG. 5 is a longitudinal view showing the manner in which the two main portions of the syringe of the instant invention are separated.
Figure 4:
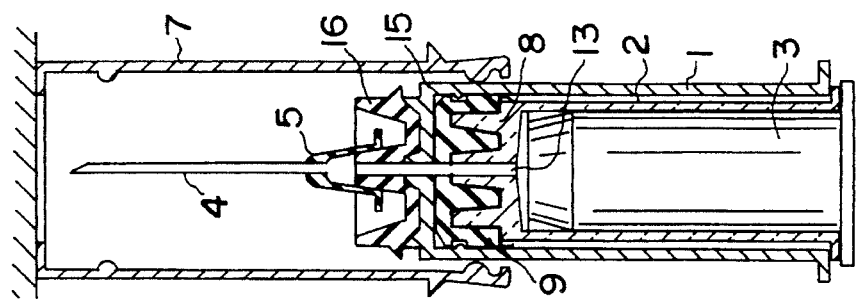
FIG. 4 is a longitudinal sectional view similar to FIG. 3, wherein the needle is shown retracted after use.

The disposable character of the syringe of the present invention is shown clearly in FIGS. 4 and 5, wherein the sections comprising the syringe can be separated and discharged. Due to needle cover 7, the user can avoid contact with the needle or the surrounding area after the injection. That is, the needle cover 7 is designed to engage plug 16, which is connected with needle plugging cone 5, at the end of its stroke, as shown in FIG. 5. Once engaged, the entire cover 7 with needle 4 can be removed from main body 1 and discarded.

The primary advantage of this invention is that a double chamber syringe is provided having means for mixing substances in each of the chambers without contaminating the resulting mixture. Another advantage is that a double chamber syringe is provided wherein the chambers are separated by a pressure breachable sheet. Yet another advantage is that a double chamber syringe is provided having a pressure breachable sheet extending between two chambers of the syringe, wherein the syringe includes an internal design for directing a fluid under high pressure at the sheet.

It is apparent that there has been provided in accordance with this invention a double chamber disposable syringe which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A double chamber disposable syringe, comprising:

a main hollow body having an inner diameter and engaged with an injection needle;

a second hollow body having an outer diameter smaller than the inner diameter of the main body and adapted to be moved relative to the main body, the second hollow body having an open lower end and an upper end, wherein the upper end defines a plugging means;

a plunger means engaged with and movable in the second body for creating a pressure in the second body, the plunger means projecting through the open lower end of the second hollow body wherein the second hollow body is positioned substantially between the main body and the plunger means;

a plug engaged with the inner diameter of the main body and located adjacent the plugging means, wherein the plug and plugging means have conduits in substantial alignment, the conduit of the plug leading into the main body and the conduit of the plugging means leading into the second body; and a sheet means for separating the conduits of the plug and plugging means positioned between the conduits of the plug and plugging means, wherein the sheet means is penetrable via the pressure created by the plunger means in the second body.

2. The syringe according to claim 1, wherein upon the application of the pressure against the sheet means, the sheet means is adapted to cleanly puncture substantially without the separation of contaminable particles therefrom.

3. The syringe according to claim 2, wherein the sheet means is formed from rubber.

4. The syringe according to claim 1, wherein the conduit of the plugging means has a first diameter and extends from the sheet means and into the second hollow body having an inner diameter substantially larger than the conduit for causing increased pressure for penetrating the sheet means.

5. The syringe according to claim 1, wherein a second pressure is created in the main body via the second hollow body moving relative to the main body, further comprising a second sheet means for separating the main body from the needle, the second sheet means being penetrable via the second pressure.

6. The syringe according to claim 5, further comprising a secondary plug means positioned in the main body at an end opposite the positioning of the first plug means and a secondary plug engaged with the plug means and positioned between the main body and the needle, wherein the second sheet means is positioned between the secondary plug means and the secondary plug.

7. The syringe according to claim 6, wherein each of the secondary plug means and plug has a conduit wherein the conduit of the secondary plug means is in substantial alignment with the conduit of the secondary plug, the sheet means being positioned between the conduits.

8. The syringe according to claim 1, further comprising a cylindrical needle cover extending from the main body and slidably engaged with the main body for enclosing the needle.

9. The syringe according to claim 5, wherein upon the application of the second pressure against the second sheet means, the second sheet means is adapted to puncture substantially without the separation of contaminable particles therefrom.

* * * * *